US00PP11233P

United States Patent [19]

Jacob

[11] Patent Number: Plant 11,233

[45] Date of Patent: Feb. 22, 2000

[54] *PRUNUS PUMILA* DWARFING ROOTSTOCK NAMED 'RENUS 2'

[75] Inventor: Helmut B. Jacob, Geisenheim, Germany

[73] Assignee: Tree Connection, Inc., Dundee, Oreg.

[21] Appl. No.: 08/961,568

[22] Filed: Oct. 30, 1997

[51] Int. Cl.[7] ..... A01H 5/00

[52] U.S. Cl. ..... Plt./183

[58] Field of Search ..... Plt./37, 36, 35.2, Plt./38.1, 38.2, 39, 40.1, 41.1, 41.2, 41.3, 41.4, 42.1, 43.1, 43.2, 43.3, 183

*Primary Examiner*—Howard J. Locker
*Assistant Examiner*—Anne Marie Grünberg
*Attorney, Agent, or Firm*—Klarquist Sparkman Campbell Leigh & Whinston, LLP

[57] ABSTRACT

*Prunus pumila* variety 'Rhenus 2' is a dwarfing rootstock that is compatible with Prunus varieties such as peach, nectarine, and apricot, producing dwarf trees with no significant reduction in fruit size, early yield, high yield efficiency, uniform fruit size, high frost hardiness, no suckering, and good soil adaptation.

1 Drawing Sheet

BACKGROUND OF THE INVENTION

The present invention comprises a new variety of sand cherry, or dwarf cherry (*Prunus pumila*), referred to by the varietal name 'Rhenus 2'. 'Rhenus 2' is useful, for example, as a rootstock for peach, nectarine, apricot, and other Prunus varieties, displaying good compatibility and producing dwarf trees with high yield efficiency and high frost hardiness, thus allowing such varieties to be grown in colder climates.

The new variety was selected by me in a cultivated area in an orchard at the Research Station of Viticulture and Horticulture in Geisenheim, Germany. At the Research Station, fifty-five *Prunus pumila* seedlings resulting from open pollination of a *Prunus pumila* maternal parent were selected for testing. Five peach varieties ('Sunglo', 'Sunking', 'Red Haven', 'Fair Haven', and 'Hale Berta Giant') were grafted to rootstock of these seedlings and to the rootstock 'Nemaguard' for comparison purposes. Fifteen trees of each of the grafted varieties were observed from 1986 to 1995 with regard to the following parameters: trunk cross-sectional area, cumulative marketable yield, yield efficiency, blossoming (from 1987 to 1995), tree health, compatibility, frost hardiness, suckering, soil adaptation. Clone 73/95 was one of the seedling clones with the best results.

In 1994, a second trial was performed. Thirty trees from each of four peach varieties ('Suncrest', 'Early Red Haven', 'Hale Berta Giant', and 'Redcal') and seventeen trees from each of three apricot varieties ('Orangered', 'Hargrand', and 'Harlayne') were grafted to rootstock from selected *Prunus pumila* seedlings from the first evaluation and to 'Nemaguard' rootstock for comparison purposes. Clone 73/95 displayed the best results of the seedlings tested and was renamed 'Rhenus 2'.

'Rhenus 2' has not been observed under all possible environmental conditions and its phenotype may vary significantly with variations in environment such as temperature, light intensity, and daylength, without any variation in genotype. However, the following unique combination of characteristics have been repeatedly observed in asexually propagated progeny of 'Rhenus 2' and distinguish it from all other varieties: (1) causes substantial dwarfing when used as a rootstock for peach, nectarine, and apricot scions with no significant reduction in fruit size; (2) compatibility as a rootstock with a wide variety of peach, nectarine, and apricot varieties; (3) when used as a rootstock, provides an early yield, high yield efficiency, substantially uniform fruit size, high frost hardiness, no suckering, and good soil adaptation. These characteristics are established and transmitted through succeeding asexual propagations.

Asexual reproduction of 'Rhenus 2' was performed by hardwood cuttings, softwood cuttings (e.g., tips and intermediate cuttings), stool bed propagation (layering), and tissue culture. Asexual propagation has been accomplished in McMinnville, Oreg. and elsewhere in Germany. Other conventional methods for propagation of *Prunus pumila* varieties may also be used. Best results have been observed with hardwood cuttings (quick dipping using 4000 ppm indole-3-butyric acid [IBA]).

BRIEF DESCRIPTION OF THE DRAWINGS

The following drawings are photographs of 'Rhenus 2' taken at the Research Station of Viticulture and Horticulture in Geisenheim, Germany, in September 1995.

DETAILED DESCRIPTION

The following is a detailed description of the invention based on plants grown at the Research Station of Viticulture and Horticulture in Geisenheim, Hessen, Germany. Color descriptions and other terminology are used herein in accordance with ordinary dictionary significance or as commonly used by those of ordinary skill in the relevant art, unless otherwise noted with reference to The Royal Horticultural Society Colour Chart (R.H.S.). It should be noted that color will vary with time of year, lighting and growing conditions. For example, leaves tend to be brighter green if grown in soil with a high nitrogen content and more yellow if grown in soil with lower nitrogen content.

All 'Rhenus 2' trees, insofar as I have been able to observe them, have been identical in all the characteristics described below.

Propagation: Holds to distinguishing characteristics through succeeding propagation by rooted cuttings.

Figure 2:
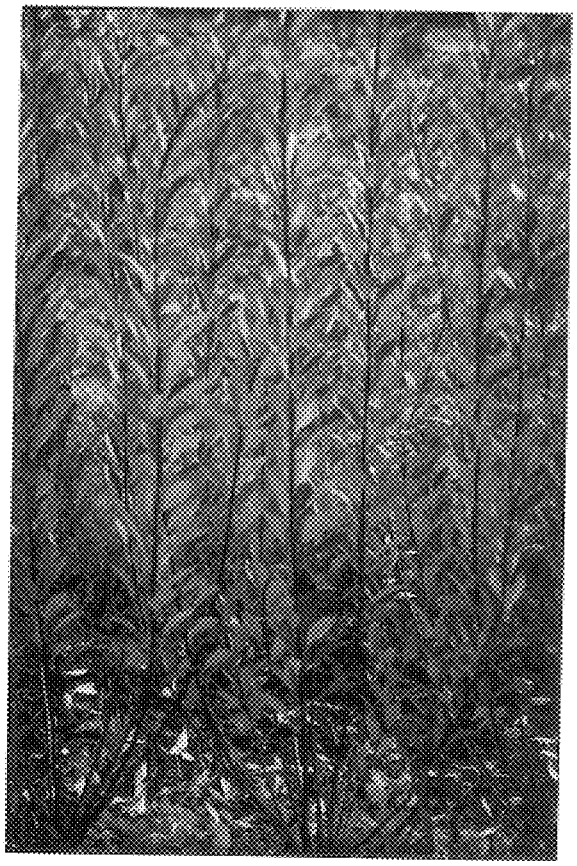
FIG. 2 is a view of two-year-old nongrafted specimens of 'Rhenus 2'.
Figure 3:
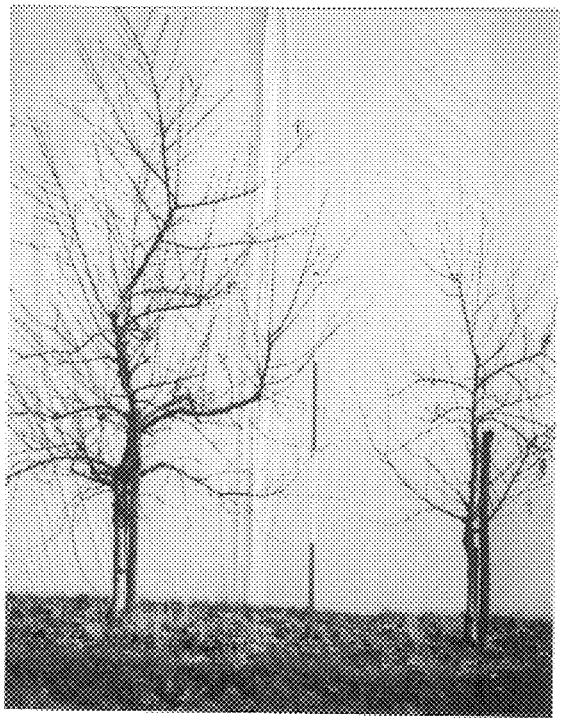
FIG. 3 is a view of five-year-old 'Red Haven' trees grown on 'Nemaguard' rootstock (left) and 'Rhenus 2' rootstock (right).

Tree:

*Trunk.*—Size: FIG. 2 provides a view of typical two-year-old nongrafted specimens. FIG. 3 provides a view of five-year-old 'Red Haven' trees grown on 'Rhenus 2' rootstock (right) and, for comparison purposes, on 'Nemaguard' rootstock (left). The trunk caliper on two year old tree growing in Dundee, Oreg., was one-eighth inch measured about one inch above the ground. Surface texture: Smooth. Bark color: Bright gray-brown (like R.H.S. 178C on one year old trunk and R.H.S. 177A on two year old trunk, growing in Dundee, Oreg.).

*Form.*—Spread upright, later semi-erect.

*Branches.*—Surface texture: Smooth. Bark color: Red-brown. New growth color: Bright green. Mature growth color: Red-brown. Like R.H.S. 175A on mature one year branches. Mature one year branches are those that have matured over the summer of a single growing season. Internode length: 15–20 mm. Lenticels: Yellow-white, pointed-rounded (like R.H.S. 163C). Bud: Color observed in spring in Dundee, Oreg., was brown, like R.H.S. 177B.

Figure 1:
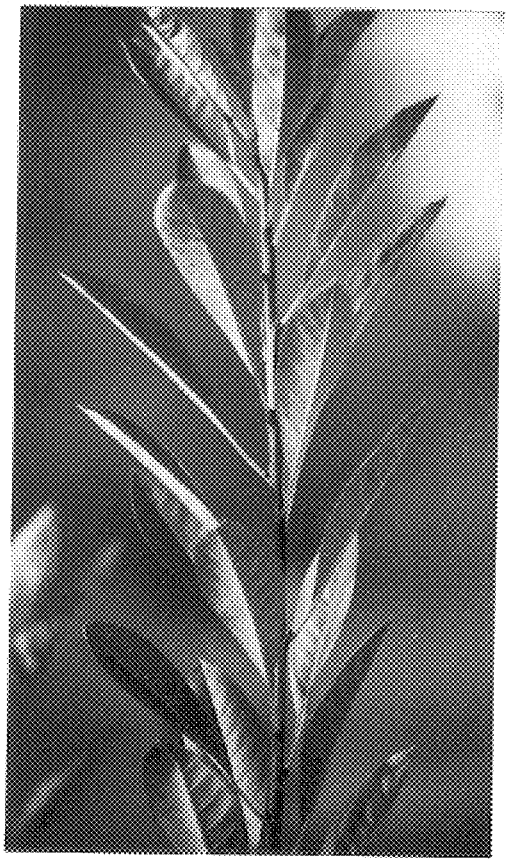
FIG. 1 is a view of a typical twig and leaves of 'Rhenus 2'.

*Leaves.*—(see FIG. 1). Size: Generally small. Length averages 70–80 mm, including the petiole. Width averages 20–25 mm. Surface texture: Normal for the species. Form: Linear elongated. Color: Upper surface is bright to dark green (Like R.H.S. 137D when observed in Dundee, Oreg. in the spring). Lower surface is bright gray-green (Like R.H.S. 139C when observed in Dundee, Oreg. in the spring). Mid-vein: Size: average. Color: yellow-green. Petiole: Length normal for species, 10–15 mm. Thickness 0.2–0.3 mm. Color is yellow-green to green (Like R.H.S. 137D when observed in Dundee, Oreg. in the spring). No leaf glands observed.

*Flowers.*—Size: Small, about 5 mm in diameter. Color: White (Like R.H.S. 155C). Number: 2–4 per bud. Fragrance: Very weak. Sexual characteristics: Flower is complete, fertile, but self-unfruitful.

*Fruit.*—No fruit borne by 'Rhenus 2' trees in six years of observation.

Soil adaptation and tolerance:

*Chlorosis.*—No problems observed.

*Wet.*—No problems observed.

Multiplication ability:

*Layering.*—Good.

*Hardwood cuttings* (*with IBA*).—Very good.

*Softwood cuttings* (*with IBA*).—Very good.

Pathogen resistance:

*Fungal disease.*—No problems observed.

*Insects.*—No problems observed.

*Mites.*—No problems observed.

*Viruses.*—No problems observed. Non-host for plum pox (Sharka)-virus.

*Diseases.*—No problems observed.

Performance as rootstock when grafted:

*Root sprouts* (*suckering*).—None in nine years.

*Anchorage.*—Very good.

*Compatibility.*—Very good. No incompatibility observed with any peach or nectarine variety. No incompatibility with apricots after four years' testing. Compatibility expected with most other Prunus species, although incompatible with at least some varieties of European plums.

*Vigor.*—Dwarfing. Prunus tree scions grafted to 'Rhenus 2' rootstock are approximately 70–80% as vigorous as when grafted to 'Nemaguard' rootstock.

'Rhenus 2' is useful, for example, as a dwarfing rootsock with peaches, nectarines, and apricots (*P. armeniaca*), as well as with other Prunus species such as plums (e.g., *P. domestica, P. salicina*). Although incompatibility has been observed with some varieties of European plums, 'Rhenus 2' is compatible with all varieties of peaches, nectarines, and apricots that have been tested and no graft line problems have been observed. For example, the trunk circumference of a 'Red Haven' scion grafted to 'Rhenus 2' rootstock is reduced by about 34 percent compared to a 'Red Haven' scion grafted to 'Nemaguard' rootstock (155 mm and 235 mm, respectively) (Table 1). 'Nemaguard' is an unpatented rootstock which is commercially available.

Also, the yield efficiency of 'Red Haven' peach scions on 'Rhenus 2' rootstock is approximately 52 percent higher than 'Red Haven' peach scions on 'Nemaguard' rootstock (Table 1). Scions grafted to 'Rhenus 2' also display early yield or precocity (i.e., a cumulative marketable yield of fruit of a variety grafted to 'Rhenus 2' rootstock that is significantly higher five or six years after planting as compared with the same scion variety grafted to a reference rootstock).

In general, the yield of a Prunus scion grafted to 'Rhenus 2' rootstock is about one year earlier than when grafted to 'Nemaguard' rootstock. Moreover, 'Rhenus 2' displays high frost hardiness.

In a cold treatment trial, 'Rhenus 2' exhibited no observable damage when subjected to a temperature of −15° C. for fifteen days, while other peach rootstock selections died or were severely injured.

Comparison Tables

The following tables provide data regarding the growth of peach varieties grafted as scions to 'Rhenus 2' and comparisons of the Red Haven peach variety grafted to both 'Rhenus 2' and 'Nemaguard' rootstock. No significant fruit size differences or graft line problems were observed. Measurements are made 10–20 cm above the bud union on grafted trees.

TABLE 1

Trunk Circumference and Tree Head Volume of Peach Varieties Grafted to 'Rhenus 2' or 'Nemaguard' Rootstock Five Years After Planting

| Variety | Rootstock | Tree Circumference (mm) | Tree Head Volume ($m^3$) |
|---|---|---|---|
| Sunglo | Rhenus 2 | 176 | 1.2 |
| Sunking | Rhenus 2 | 173 | 1.2 |
| Fairhaven | Rhenus 2 | 143 | 1.0 |
| Hale Berta Giant | Rhenus 2 | 157 | 1.2 |
| Red Haven | Rhenus 2 | 155 | 1.2 |
| Red Haven | Nemaguard | 235 | 5.3 |

TABLE 2

Yield Efficiency/Productivity and Fruit Weight of Red Haven Grafted to 'Rhenus 2' and 'Nemaguard' Rootstock

| Variety | Rootstock | Yield Efficiency* | Fruit Weight (g)** |
|---|---|---|---|
| Red Haven | Rhenus 2 | 79 | 96 |
| Red Haven | Nemaguard | 52 | 106 |

*Total yield 1986–1991 (kg) divided by trunk circumference (mm).
**Average of four years.

I claim:

1. A new and distinct variety of *Prunus pumila* plant as herein shown and described.

* * * * *